United States Patent [19]

Schmidt, III

[11] Plant 4,987

[45] Mar. 1, 1983

[54] FLOWERING PLUM TREE

[76] Inventor: J. Frank Schmidt, III, 14131 SE. 312th, Boring, Oreg. 97009

[21] Appl. No.: 275,715

[22] Filed: Jun. 22, 1981

[51] Int. Cl.[3] ..... A01H 5/12

[52] U.S. Cl. ..... Plt./38

[58] Field of Search ..... Plt./38

*Primary Examiner*—Robert E. Bagwill

*Attorney, Agent, or Firm*—Klarquist, Sparkman, Campbell, Leigh, Whinston & Dellett

[57] ABSTRACT

This invention relates to a novel variety of Newport Plum Tree, distinguished by its more vigorous growth rate, larger foliage, heavier branching and redder coloration of the entire tree.

1 Drawing Figure

DESCRIPTION

The present invention relates to a new and distinct variety of flowering plum tree of the species botanically known as *Prunus cerasifera Newport,* and commonly called "Newport Plum."

I discovered my new variety, believed to be a result of a bud sport, among a group of nursery trees of the Newport Plum variety which were being grown in a cultivated area of a nursery in Milton-Freewater, Oreg. These trees had been budded approximately two years earlier on Myrobalam Plum (*Prunus myrobalana,* otherwise known as *Prunus cerasifera*) understock. My attention was first attracted to the new tree because of its unique appearance. More specifically, at that time, my new tree appeared taller than other trees in the group. In addition, the foliage of my new tree appeared larger and the tree seemed brighter red in color, in comparison to surrounding trees.

Close observation of the parent tree, asexual reproduction of the parent tree under my direction to produce progeny thereof, continued observations of such progeny, which possessed identical characteristics so far as observable and which were subsequently asexually propagated under my direction and control by budding, has convinced me that my new tree represents a new and improved variety of Newport Plum tree. Furthermore, these observations have confirmed that my new variety is particularly evidenced by the following unique combination of characteristics, which have proven firmly fixed, are outstanding therein and which distinguish it from all other varieties of this species, of which I am aware:

1. Rapid, vigorous rate of growth;
2. Extremely large leaves;
3. Heavier branching, particularly during the first growing season following budding; and
4. A redder appearing tree.

In determining the above characteristics, I have compared my new tree with common Newport Plum trees, which were growing under the same conditions, in a nursery plot located near Canby, Oreg.

The accompanying photographs depict the color of the foliage of my new variety as nearly true as is reasonably possible to make the same in a color illustration of this character.

FIG. 1 is a color photograph of portions of two trees of the present invention taken in the spring of 1980.

The primary distinguishing feature of my new tree, over other trees of this species, is its much more vigorous rate of growth. More specifically, in some early observations of young trees of my variety, it was noticed that they were taller than other trees of this species of the same age which were growing in the same area. Subsequent visual observations of progeny of my new variety confirmed this faster growing characteristic. In addition to such visual observations, during the 1980 growing season, spring and summer, measurements were made of the growth of two-year-old trees of my new variety and of the growth of common Newport Plum trees of the same age. These measurements were made of trees of my new variety and of trees of the common variety which were growing in an adjacent row in a nursery. All of these trees were budded on Myrobalam Plum understock.

More specifically, in mid-November of 1980, the caliper of twenty-five trees of the common variety was measured at a point approximately three inches above the location of budding to the understock. The average caliper of these trees was approximately 1.7 centimeters. Similar measurements were made of the caliper of twenty-five trees of my new variety, growing in the adjacent row. The average caliper of these trees of my new variety was 2.3 centimeters.

In addition, measurements were made on June 4, July 7, Aug. 4 and Sept. 4, 1980 of the length of side branches of my new variety of Newport Plum tree, and of the length of side branches of common Newport Plum trees. On each date, fifty branches from trees of my new variety were measured. Also, on each date, fifty branches from trees of the common variety were measured. These branches were located at approximately the same position on the trees. Again, the trees were located in an adjacent row in a nursery. The following table summarizes the average of these measurements.

| AVERAGE LENGTH OF SIDE BRANCHES | | |
|---|---|---|
| DATE | NEW NEWPORT PLUM TREE | COMMON NEWPORT PLUM TREE |
| June 4, 1980 | 96.4cm | 74.5cm |
| July 7, 1980 | 98.2cm | 88.0cm |
| August 4, 1980 | 106.6cm | 95.2cm |
| Sept. 4, 1980 | 108.6cm | 88.8cm |

Although only a limited number of samples were taken, and the results of the Aug. 4, 1980 measurements of common Newport Plum trees seem somewhat inconsistent, the measurements do confirm my observations that my new Newport Plum tree is a much faster growing tree than common Newport Plum trees.

Also, as mentioned previously, the foliage of my new tree is larger than the foliage of common Newport Plum trees. In addition to my visual observations, during the 1980 growing season, measurements and comparisons were made of the size of foliage of my new tree with the size of foliage of common Newport Plum trees growing in an adjacent row of a nursery. Although there is naturally a variation from leaf to leaf, typical leaves of my Newport Plum trees averaged 92 millimeters long and 47 millimeters wide. In contrast, leaves of the common Newport Plum trees had typical average lengths of 70 millimeters and widths of 33 millimeters. Thus, the foliage of my new tree is significantly larger than the foliage of common trees of this species, thereby enhancing the ornamental appearance of my new tree.

Also, my new variety of Newport Plum tree is heavier branching, particularly during the first growing season. By heavier branching, it is meant that the new tree branches earlier. Typically, during the first year following budding, many of my new Newport Plum trees will form side branches. In contrast, very few common Newport Plum trees form side branches during the first growing season after budding. Because of this heavier branching characteristic, which seems associated with the faster growth rate of my new tree, the new tree assumes a desirable ornamental appearance earlier in life.

In addition, when viewed in its entirety, it appears to me that my new tree is redder in color than common Newport Plum trees. This redder color, in fact, initially was one reason I found my new tree. However, although the entire tree appears to be more red in color, individual leaves of my new tree do not seem significantly different in color from individual leaves of prior Newport Plum trees.

Otherwise, insofar as I have been able to observe, at this time, my new variety is believed generally typical of the species.

The following is a detailed description of my new variety of *Prunus cerasifera Newport* tree, with color terminology in accordance with The Royal Horticultural Society Colour Chart (hereinafter R.H.S.), published by The Royal Horticultural Society of London. It is pointed out, however, the coloration of the leaves, as indicated below, is only approximate because the coloration varies considerably depending on lighting conditions and the time of year. In addition, the size and shape of leaves varies depending upon the nature of the growing season.

Parentage: Believed a bud sport of *Prunus cerasifera Newport.*

Propagation: Holds to distinguishing characteristics through succeeding propagation by budding on Myrobalam Plum understock.

Locality where grown and observed: Milton-Freewater, Oreg. and Canby, Oreg.

Tree: Upright, rapid growing.

Foliage:

*Shape.*—Ovate, with some leaves being broader than others.

*Apex.*—Accuminate.

*Base.*—Obtuse.

*Margin.*—Crenate.

*Size.*—Typically 92 mm long and 47 mm broad.

*Color.*—In early summer, the immature leaves are a maroon color like R.H.S. plate 178A, the somewhat older leaves are a deep red-purple color like R.H.S. plate 187A and the mature leaves are a deep green color like R.H.S. plate 147A. In the fall, the leaves are a deep red-purple color like R.H.S. plate 187A.

I claim:

1. A new and distinct variety of flowering plum tree substantially as herein shown and described, characterized particularly as a novelty by a vigorous rate of growth, large foliage, heavier branching and red coloration.

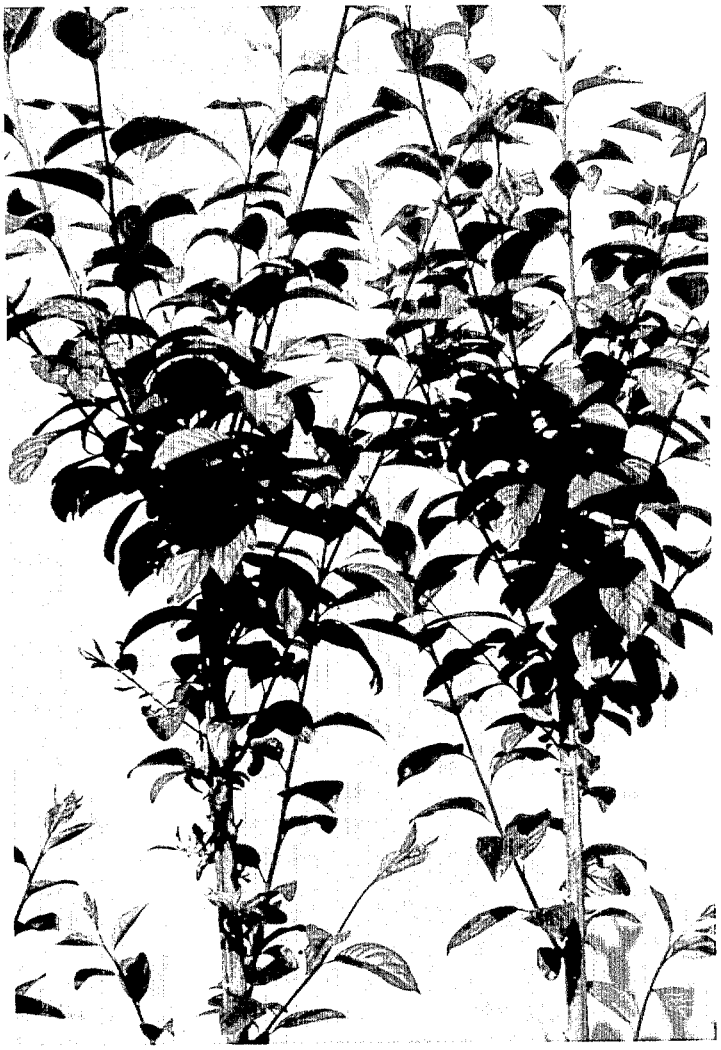

* * * * *